US006077514A

United States Patent [19]
Maassab et al.

[11] Patent Number: 6,077,514
[45] Date of Patent: Jun. 20, 2000

[54] ATTENUATED RESPIRATORY SYNCYTIAL VIRUS

[75] Inventors: Hunein F. Maassab; M. Louise Herlocher, both of Ann Arbor, Mich.

[73] Assignee: The Regents of the University of Michigan, Ann Arbor, Mich.

[21] Appl. No.: 08/882,358

[22] Filed: Jun. 25, 1997

Related U.S. Application Data

[63] Continuation-in-part of application No. PCT/US97/05588, Apr. 3, 1997.
[60] Provisional application No. 60/014,848, Apr. 4, 1996.
[51] Int. Cl.$^7$ .............................. A61K 39/155; C12N 7/01
[52] U.S. Cl. ...................... 424/211.1; 424/9.2; 435/235.1
[58] Field of Search .......................... 435/235.1; 424/9.2, 424/211.1

[56] References Cited

U.S. PATENT DOCUMENTS

| 4,122,167 | 10/1978 | Buynak et al. ...................... 424/211.1 |
| 4,800,078 | 1/1989 | Prince et al. . |
| 5,223,254 | 6/1993 | Paradiso et al. . |

OTHER PUBLICATIONS

Ambrose, M.W. et al., "Evaluation of the immunogenicity and protective efficacy of a candidate parainfluenza virus type 3 subunit vaccine in cotton rats," *Vaccine* 9:505–511 (1991).
Anderson, L.J. et al., "Antigenic Characterization of Respiratory Syncytial Virus Strains with Monoclonal Antibodies," *J. Inf. Dis.* 151:626–633 (1985).
Anderson, L.J. et al., "Multicenter Study of Strains of Respiratory Syncytial Virus," *J. Inf. Dis.* 163:687–692 (1991).
Belshe, et al., "Evaluation of a Live Attenuated cold–Adapted Parainfluenza Virus Type 3 Vaccine in Children," *Journal of Clinical Microbiology* 30(8):2064–2070 (1992).
Brideau, et al., "Protection of cotton rats against human parainfluenza virus type 3 by vaccination with a chimeric FHN subunit glycoprotein," *Journal of General Virology* 74:471–477 (1993).
Chanock, et al., "Serious Respiratory Tract Disease Caused by Respiratory Syncytial Virus: Prospects for Improved Therapy and Effective Immunization," *Pediatrics* 90(1):137–143 (1992).
Cherrie, et al., "Human Cytotoxic T Cells Stimulated by Antigen on Dendritic Cells Recognize the N, SH, F, M, 22K and 1b Proteins of Respiratory Syncytial Virus," *Journal of Virology* 66(4):2102–2110 (1992).
Chin, J. et al., "Field Evaluation Of A Respiratory Syncytial Virus Vaccine And A trivalent Parainfluenza Virus Vaccine In A Pediatric Population," *Am. J. Epidemiol.* 89:449–463 (1969).
Clements, M.L. et al., "Evaluation of Bovine, Cold–Adapted Human, and Wild–Type Human Parainfluenza Type 3 Viruses in Adult Volunteers and in Chimpanzees," *J. Clin. Microbiol.* 29:1175–1185 (1991).

Connors, M. et al., "Cotton rats previously immunized with a chimeric RSV FG glycoprotein develop enhanced pulmonary pathology when infected with RSV, a phenomenon not encountered following immunization with vaccinia—RSV recombinants or RSV," *Vaccine* 10(7):475–484 (1992).
Connors, M. et al., "Pulmonary Histopathology Induced by Respiratory Syncytial Virus (RSV) Challenge of Formalin–Inactivated RSV–Immunized BALB/c Mice Is Abrogated by Depletion of CD4$^+$ T Cells," *Journal of Virology* 66(12):7444–7451 (1992).
Connors, M. et al., "Enhanced Pulmonary Histopathology Induced by Respiratory Syncytial Virus (RSV) Challenge of Formalin–Induced RSV–Immunized BALB/c Mice Is Abrogated by Depletion of Interleukin–4 (IL–4) and IL–10," *Journal of Virology* 68(8):5321–5325 (1994).
Ebata, S.N. et al., "Function and immunogenicity of human parainfluenza virus 3 glycoproteins expressed by recombinant adenoviruses," *Virus Research* 24:21–33 (1992).
Edwards, K.M. et al., "Safety and Immunogenicity of Live Attenuated Cold–Adapted Influenza B/Ann Arbor/1/86 Reassortant Virus Vaccine in Infants and Children," *J. Inf. Dis.* 163:740–745 (1991).
Ewasyshyn, M. et al., "Comparative analysis of the immunostimulatory properties of different adjuvants on the immunogenicity of a prototype parainfluenza virus type 3 subunit vaccine," *Vaccine* 10(6):412–420 (1992).
Fulginiti, V.A. et al., "Respiratory Virus Immunization," *Am. J. Epidemiol.* 89:435–448 (1969).
Glezen, W.P. et al., "Risk of respiratory syncytial virus infection for infants from low–income families in relationship to age, sex, ethnic group, and maternal antibody level," *J. Ped.* 98(5):708–715 (1981).
Glezen, W.P. et al., "Risk of Primary Infection and Reinfection With Respiratory Syncytial Virus," *Am. J. Dis. Child.* 140:543–546 (1986).
Glezen, et al., Appendix N. *Prospects For Immunizing Against Respiratory Syncytial Virus*, pp. 397–409.
Gupta, A. et al., "Restoration of Suppressor T–Cell Functions in Children With AIDS Following Intravenous Gamma Globulin Treatment," *AJDC* 140:143–146 (1986).
Hall, S.L. et al., "Cold–passaged human parainfluenza type 3 viruses contain ts and non–ts mutations leading to attenuation in rhesus monkeys," *Virus Research* 22:173–184 (1992).
Hall, C.B. et al., "Immunity to and Frequency of Reinfection with Respiratory Syncytial Virus," *J. Inf. Dis.* 163:693–698 (1991).

(List continued on next page.)

*Primary Examiner*—Mary E. Mosher
*Assistant Examiner*—Ali R. Salimi
*Attorney, Agent, or Firm*—Lahive & Cockfield; DeAnn F. Smith

[57] ABSTRACT

Attenuated respiratory syncytial viruses (RSV) and in particular temperature sensitive RSV are provided. The viruses of the present invention may be used in pharmaceutical compositions such as vaccines. Methods of making and using such pharmaceutical compositions are also provided.

7 Claims, 5 Drawing Sheets

OTHER PUBLICATIONS

Hall, et al., "A Cold–Adapted Mutant of Parainfluenza Virus Type 3 Is Attenuated and Protective in Chimpanzees" *Journal Infectious Disease* 167:958–962 (1993).

Hall, S.L. et al., "Protection of cotton rats by immunization with the human parainfluenza virus type 3 fusion (F) glycoprotein expressed on the surface of insect cells infected with a recombinant baculovirus," *Vaccine* 9:659–667 (1991).

Henderson, F.W. et al., "Respiratory–Syncytial–Virus Infections, Reinfections And Immunity," *N. Eng. J. Med.* 300:530–534 (1979).

Jensen, et al., "Immunization Against Parainfluenza Infections," *Department of Biologics Research*, Chas. Pfizer & Co., Inc., 89:216–226 (Dec. 1961).

Kapikian, A.Z. et al., "An Epidemiologic Study Of Altered Clinical Reactivity To Respiratory Syncytial (RS) Virus Infection In Children Previously Vaccinated With An Inactivated RS Virus Vaccine," *Am. J. Epidemiol.* 89:405–421 (1968).

Kasel, J.A. et al., "Acquisition Of Serum Antibodies To Specific Viral Glycoproteins Of Parainfluenza Virus 3 In Children," *Journal of Virology* 52(3):828–832 (1984).

Kasel, et al., "Relation of Serum Antibody to Glycoproteins of Respiratory Syncytial Virus with Immunity to Infection in Children," *Vir. Immunol.* 1:199–205 (1987/88).

Kim, H.W. et al., "Respiratory Synctial Virus disease In Infants Despite Prior Administration Of Antigenic Inactivated Vaccine," *Am. J. Epidemiol.* 89:422–434 (1969).

Kim, H.W. et al., "Clinical And Immunological Response Of Infants And Children To Administration Of Low–Temperature Adapted Respiratory Syncytial Virus," *Pediatrics* 48:745–755 (1971).

Kim et al., "Safety And Antigenicity Of Temperature Sensitive (TS) Mutant Respiratory Syncytial Virus (RSV) In Infants And Children," *Pediatrics* 52:56–63 (1973).

Lamprecht, C.L. et al., "Role Of Maternal Antibody In Pneumonia And Bronchiolitis Due To Respiratory Syncytial Virus," *J. Inf. Dis.* 134:211–217 (1976).

Lehman, et al., "Comparison of soluble and secreted forms of human parainfluenza virus type 3 glycoproteins expressed from mammalian and insect cells as subunit vaccines," *Journal of General Virology* 74:459–469 (1993).

Maassab, H.F. et al., "Development and characterization of cold–adapted viruses for use as live virus vaccines," *Vaccine* 3:355–369 (1985).

Maniatis, T. et al., *Molecular Cloning: a Laboratory Manual*, Cold Springs Harbor Laboratory, Cold Springs, N.Y. (1982) at pp. 387–389.

McIntosh et al., *Virology*, Second Edition, 91990, Chapter 38, *Respiratory Synctial Virus*, pp. 1045–1072.

Mufson, M.A. et al., "Two Distinct Subtypes of Human Respiratory Syncytial Virus," *J. Gen. Virol.* 66:2111–2124 (1985).

Murphy, B.R. et al., "Formalin–Inactivated Respiratory Syncytial Virus Vaccine Induces Antibodies To The Fusion Glycoprotein That Are Deficient In Fusion–Inhibiting Activity," *J. Clin. Microbiol.* 26(8):1595–1597 (1987).

Murphy, B.R. et al., "Current approaches to the development of vaccines effective against parainfluenza and respiratory syncytial viruses," *Virus Research* (Review Article) 11:1–16 (1988).

Obrosova–Serova, N.P. et al., "Evaluation in children of cold–adapted influenza B live attenuated intranasal vaccine prepared by reassortment between wild–type B/Ann Arbor/1/86 and cold–adapted B/Leningrad/14/55 viruses," *Vaccine* 8:57–60 (1990).

Prince, G.A. et al., "Immunoprophylaxis and immunotherapy of respiratory syncytial virus infection in the cotton rat," *Virus Res.* 3:193–206 (1985).

Ray, R. et al., "Microencapsulated Human Parainfluenza Virus Induces a Protective Immune Response," *The Journal of Infectious Diseases* 167:752–755 (1993).

Ray, R. et al., "Glycoproteins of Human Parainfluenza Virus Type 3: Characterization and Evaluation as a Subunit Vaccine," *The Journal of Infectious Diseases* 152(6):1219–1230 (1985).

Ray, R, et al., "Glycoproteins of Human Parainfluenza Virus Type 3: Affinity Purification, Antigenic Characterization and Reconstitution into Lipid Vesicles," *J. General Virol.* (1987) 68:409–418 (1986).

Ray, R. et al., "Intranasal Immunization of Hamsters with Envelop Glycoproteins of Human Parainfluenza Virus Type 3," *The Journal Of Infectious Diseases* 157(4):648–654 (1988).

Ray, R. et al., "Human Parainfluenza Virus Induces A Type–Specific Protective Immune Response," *The Journal Of Infectious Diseases* 162:746–749 (1990).

Ray, R, et al., "Role of Individual Glycoproteins of Human Parainfluenza Virus Type 3 in the Induction of a Protective Immune Response," *The Journal Of Infectious Diseases* 62(3):783–787 (1988).

Richardson, L.S. et al., "Evaluation of Five Temperature–Sensitive Mutants of Respiratory Syncytial Virus in Primates: I. Viral Shedding, Immunologic Response, and Associated Illness," *J. Med. Virol.* 3:91–100 (1978).

Robbins, A. et al., "Obstacles to Developing Vaccines for the Third World," *Scientific American*, Nov. 1988, pp. 126–133.

Sambrook, J. et al., *Molecular Cloning: a Laboratory Manual*, Second Edition, Vol. 2, Cold Springs Harbor Laboratory, Cold Springs, N.Y., at pp. 8.46–8.47 (1989)).

Tristram, D.A. et al., "Respiratory Syncytial Virus Vaccines: Can We Improve on Nature?," *Pediatric Annals*, Dec. 1993, pp. 715–718.

van Wyke Coelingh et al., "Attenuation of Bovine Parainfluenza Virus Type 3 in Nonhuman Primates and Its Ability to Confer Immunity to Human Parainfluenza Virus Type 3 Challenge," *The Journal of Infectious Diseases* 157(4):655–662 (1988).

Walsh, E.E. et al., "Immunization with Glycoprotein Subunits of Respiratory Syncytial Virus to Protect Cotton Rats Against Viral Infection," *The Journal Of Infectious Diseases* 155(6):1198–1204 (1987).

Waris, M.E. et al., "Respiratory Syncytial Virus Infection in BALB/c Mice Previously Immunized with Formalin–Inactivated Virus Induces Enhanced Pulmonary Inflammatory Response with a Predominant Th2–Like Cytokine Pattern," *Journal of Virology* 70(5):2852–2860 (1996).

Wertz et al., *Approaches To Immunization Against Respiratory Syncytial Virus*, Chapter 7, pp. 151–176.

Wright, P.F. et al., "Administration of a Highly Attenuated, Live Respiratory Syncytial Virus Vaccine to Adults and Children," *Infect. Immun.* 37(1):397–400 (1982).

Wright, P.F. et al., "Evaluation of a live, attenuated respiratory syncytial virus vaccine in infants," *J. Pediatr.* 88:931–936 (1976) (1982).

Crowe, James E. et al., "A comparison in chimpanzees of the immunogenicity and efficacy of live attenuated respiratory syncytial virus (RSV) temperature–sensitive mutatnt vaccines and vaccinia virus recombinants that express the surface glycoproteins of RSV," *Vaccine* 11(14):1395–1404 (1993).

Martin, et al., "Epidemiology Of Respiratory Viral Infection Among Pediatric Inpatients Over A Six–Year Period In North–East England," *The Lancet* Vol. II, pp. 1035–1038 (Nov. 11, 1978).

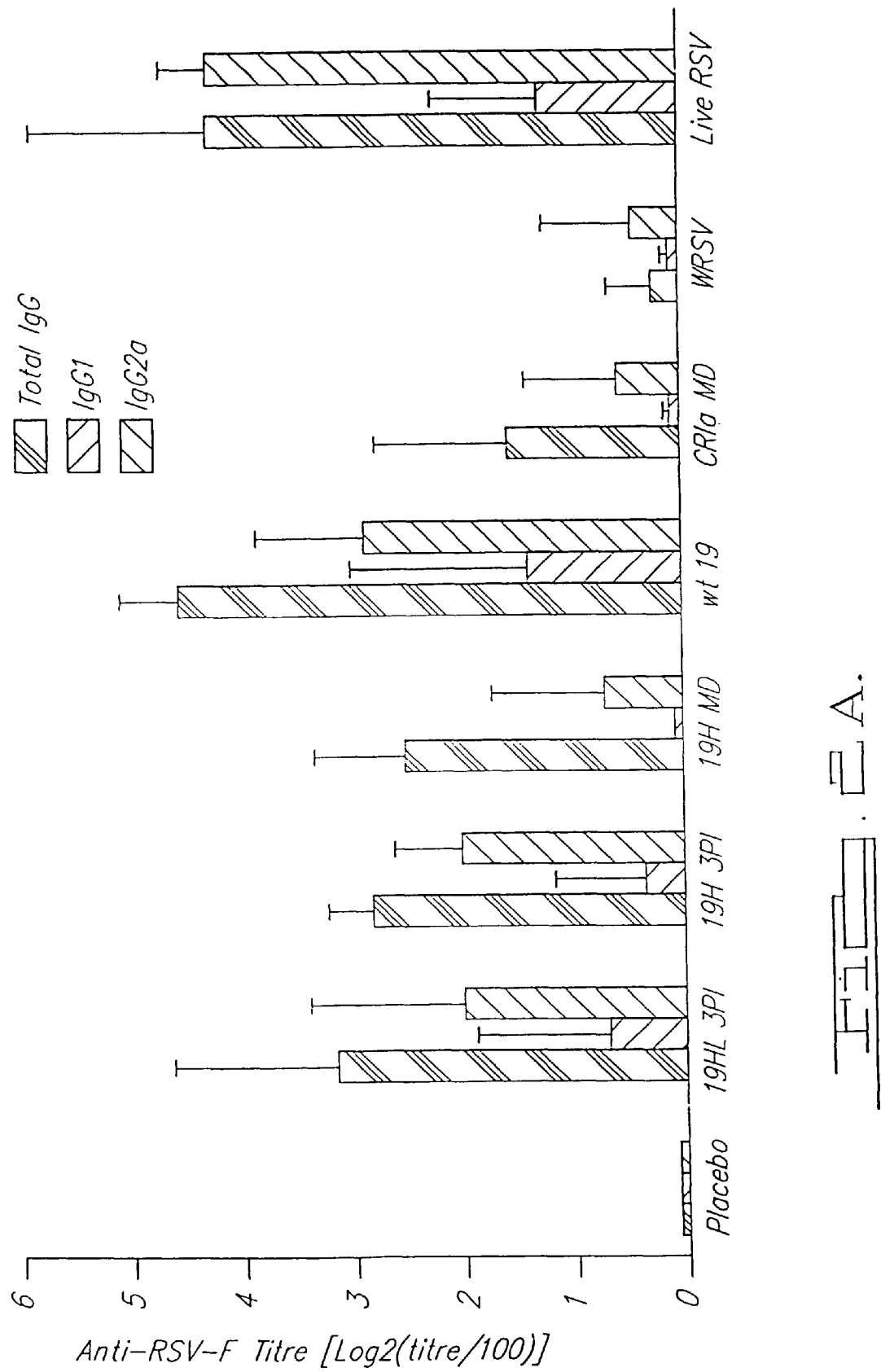

FIG. 3B.

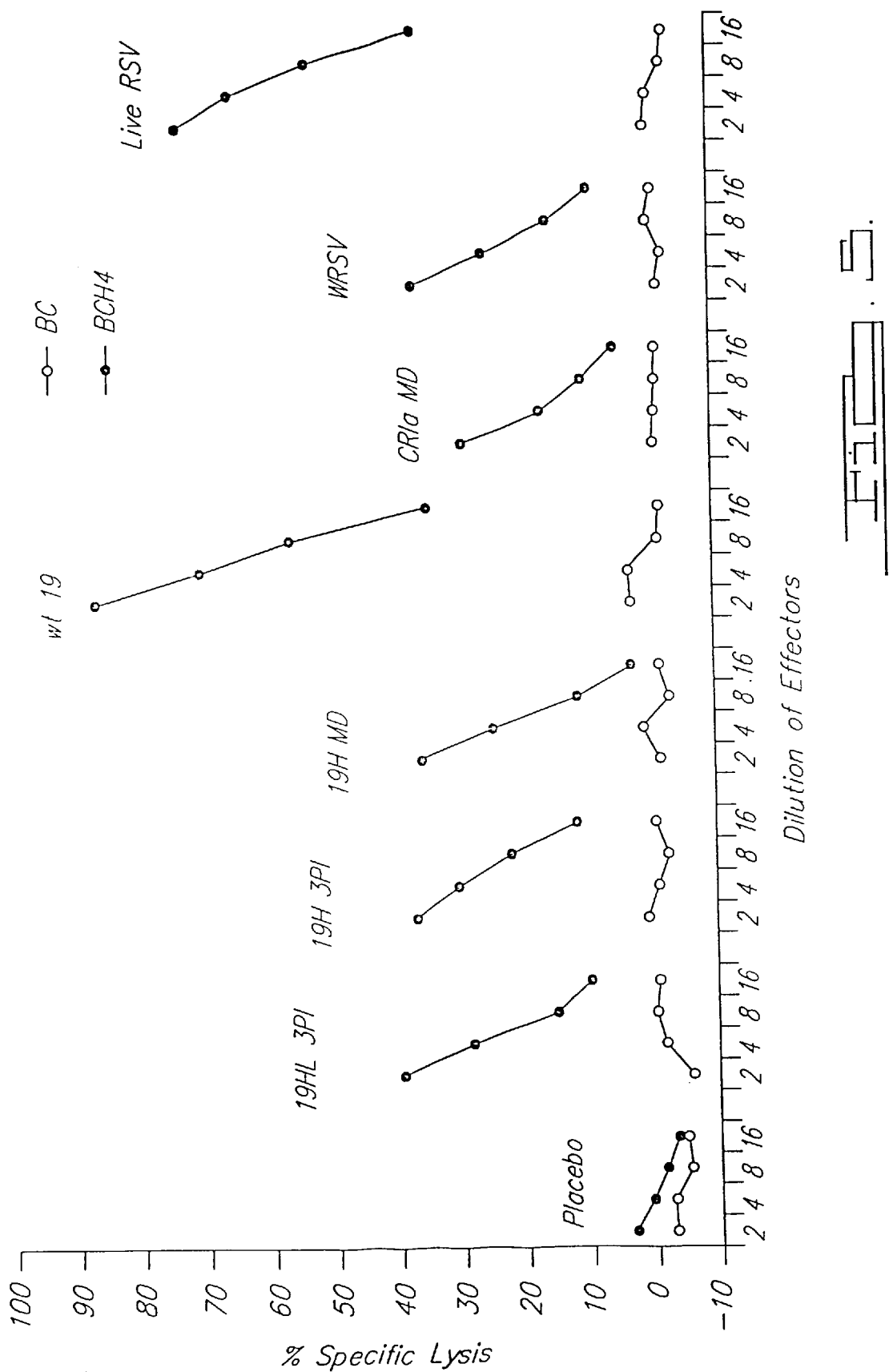

ATTENUATED RESPIRATORY SYNCYTIAL VIRUS

RELATED APPLICATIONS

The present application is a continuation-in-part of PCT International Application No. PCT/US97/05588 (designating the United States), filed Apr. 3,1997, which claims priority under 35 U.S.C. §119(e) from U.S. Ser. No. 60/014,848, filed Apr. 4, 1996. Both applications are hereby incorporated by reference.

FIELD OF THE INVENTION

The present invention relates generally to attenuated respiratory syncytial viruses and, more particularly, to live attenuated respiratory syncytial virus vaccines and methods of protecting against disease caused by infection with respiratory syncytial virus.

BACKGROUND OF THE INVENTION

Respiratory syncytial virus (RSV), a member of the paramyxoviridae family, is the leading cause of viral pneumonia and bronchitis in infants and young children worldwide, and is a major cause of fatal respiratory tract disease. Serious disease is most prevalent in infants 6 weeks to 6 months of age and in children with certain underlying illnesses (e.g., immunodeficiencies, congenital heart disease and bronchopulmonary dysplasia). Virtually all children are infected by two years of age. Most infections are symptomatic and are generally confined to mild upper respiratory tract disease. A decrease in severity of disease is associated with two or more prior infections and, in some studies, with high levels of serum antibody, suggesting that protective immunity to RSV disease will accumulate following repeated infections (Lamprecht, C. L. et al., *J. Inf. Dis.* 134:211–217 (1976); Henderson, F. W. et al., N. *Eng. J. Med.* 300:530–534 (1979); Glezen, W. P. et al., *J. Ped.* 98:706–715 (1981); Glezen, W. P. et al., *Am. J. Dis. Child.* 140:543–546 (1986); Kasel, J. A. et al., *Vir. Immunol.* 1:199–205 (1987/88); Hall, C. B. et al., *J. Inf. Dis.* 163:693–698 (1991)).

Two major subgroups of RSV have been identified, A and B, as well as antigenic variants within each subgroup (Anderson, L. J. et al., *J. Inf. Dis.* 151:626–633 (1985); Mufson, M. A. et al., *J. Gen. Virol.* 66:2111–2124 (1985)). Multiple variants of each subgroup have been found to co-circulate in epidemics which occur annually during late fall, winter, and spring months (Anderson, L. J. et al., *J. Inf. Dis.* 163:687–692 (1991)). There is evidence that children infected with one of the two major RSV subgroups may be protected against reinfection by the homologous subgroup (Mufson, M. A. et al., *J. Clin. Microbiol.* 26:1595–1597 (1987)). This, along with evidence that protective immunity will accumulate following repeated infections, suggests that it is feasible to develop an RSV vaccination regiment for infants and young children which would provide sufficient immunity to protect against disease and death.

A previous attempt to vaccinate young children against RSV employed a parenterally administered formalin-inactivated RSV vaccine. Unfortunately, administration of this vaccine in several field trials was shown to be associated with the development of a significantly exacerbated illness following subsequent natural infection with RSV (Kapikian, A. Z. et al., *Am. J. Epidemiol.* 89:405–421 (1968); Kim, H. W. et al., *Am. J. Epidemiol.* 89:422–434 (1969); Fulginiti, V. A. et al., *Am. J. Epidemiol.* 89:435–448 (1969); Chin, J. et al., Am. J. Epidemiol. 89:449–463 (1969)).

Following the lack of success with the formalin-inactivated RSV vaccine, emphasis was placed on the development of live attenuated vaccines. For example, cold adaptation, a process by which virus is adapted to grow at temperatures colder than those at which it normally optimally grows, has been used to develop temperature sensitive, attenuated RSV mutants for consideration as vaccines (Maassab, H. F. et al., *Vaccine* 3:355–369 (1985)). Unlike chemical mutagenesis in which the genetic lesions are usually single, this method generally results in the accumulation of multiple genetic lesions. These multiple lesions would help to confer phenotypic stability by reducing the probability that reversion of any one lesion will result in reversion to virulence. Stepwise cold adaptation, wherein the virus is passaged multiple times at progressively lower temperatures, has been used to successfully develop several influenza vaccine candidates currently in clinical trials (Maassab, H. F. et al., *Viral Vaccines* Wiley-Liss, Inc. (1990); Obrosova-Serova, N. P. et al., *Vaccine* 8:57–60 (1990); Edwards, K. M. et al., *J. Inf. Dis.* 163:740–745 (1991)). These mutants, which bear attenuating mutations in at least four different genes, appear to be attenuated, immunogenic, and phenotypically stable.

RSV was cold-adapted to 25–26° C. in several laboratories in the mid-1960's, but was found to be under-attenuated in vaccine trials (Kim, H. W. et al., *Pediatrics* 48:745–755 (1971); Maassab, H. F. et al., *Vaccine* 3:355–369 (1985)). However, it is of note that administration of these live RSV vaccine candidates was never associated with disease enhancement following natural infection.

Live attenuated vaccines offer several advantages over inactivated vaccines. These include the possible use of a single dose and administration by the natural route of infection i.e., intranasally. In addition, live attenuated vaccines stimulate a wide range of immune responses, including local and serum antibody responses and cellular immunity. Furthermore, these vaccines are cost-effective and can be rapidly produced and updated in the event of antigenic changes.

It would thus be desirable to provide avirulent (attenuated), immunoprotective and genetically-stable live attenuated RSV strains. It would further be desirable to provide a vaccine comprising such attenuated strains. It would further be desirable to provide methods of making and using said RSV vaccine to protect against disease caused by infection with RSV.

SUMMARY OF THE INVENTION

Attenuated RSV strains which exhibit the cold-adapted (ca) and/or temperature sensitive (ts) phenotype are provided. Samples of viruses as embodiments of the present invention have been deposited with the American Type Culture Collection (ATCC), 12301 Parklawn Drive, Rockville, Md 20582, under the terms of the Budapest Treaty, and have been accorded the following ATCC designation numbers:

TABLE 1

| Virus | Phenotype | Description | ATCC Designation No. | Date of Deposit |
|---|---|---|---|---|
| CRIa | temperature sensitive/cold-adapted | RSV, Ia-CRSV-5 CL 15 MRC27 | VR-2511 | September 20, 1995 |
| Ca19S | temperature sensitive/cold-adapted | RSV, Line 19 MRC5-15-25° st-33° | VR-2512 | September 20, 1995 |
| 19H | temperature sensitive | RSV, Line 19 MRC5-60-35° | VR-2513 | September 20, 1995 |
| Ca48V | temperature sensitive/cold-adapted | RSV, Line 48 MRC5-14-25° st MRC1-33° VERO 10-25° VERO 1-33° | VR-2514 | September 20, 1995 |
| Ca19V | temperature sensitive/cold-adapted | RSV, Line 19 MRC5-10-25° VERO 16-25° VERO 6-20° VERO 3-33° | VR-2515 | September 20, 1995 |
| CaBCV | temperature sensitive/cold-adapted | RSV, CRSV-BC5 CL-17 MRC30 | VR-2516 | September 20, 1995 |
| CaBCL | temperature sensitive/cold-adapted | RSV, CRSV-BC13 MRC19-25° MRC1-33° | VR-2517 | September 20, 1995 |
| 19H 4MD | temperature sensitive | RSV, Line 19 MRC5 92-35° C, Clone 4-1, MRC5, P-103-33° Purified by minimal limited dilution (MLD) | VR-2567 | April 2, 1997 |
| 19H 3PI | temperature sensitive/cold-adapted | RSV, Line 19 MRC 70-35° C, Vero 3-35° C., MRC5 2-35° C. Clone 2-35° C. (3PI) Plaque purified | VR-2564 | April 2, 1997 |
| 19H 5MD | temperature sensitive | RSV, Line 19 MRC5, 92-35° C. Clone 5-1 Purified by MLD | VR-2565 | April 2, 1997 |
| CRIa MD | temperature sensitive/cold-adapted | RSV, Ia-CRSV-5 MRC-38-25° C., MRC1-33° C. Purified by MLD | VR-2566 | April 2, 1997 |
| 19HL 3PI | temperature sensitive/cold-adapted | RSV, Line 19 MRC5 72-35° C. VERO 3-35° C. Large Clone 6-35° C., (3PI) Plaque Purified | VR-2572 | April 23, 1997 |
| wt 19 | | Progenitor wt RSV, line 19 MRC5 1-33° C., VERO 2-35° C., MRC5 1-35° C. Purified by MLD | VR-2570 | April 23, 1997 |
| WRSV | | Progenitor wt RSV, WI 38-3 MRC5 9-35° C., MRC5 1-35° C., Purified by MLD | VR-2571 | April 23, 1997 |

The deposit of the viruses will be maintained in the ATCC depository, which is a public depository, for a period of 30 years, or 5 years after the most recent request, or for the effective life of a patent, whichever is longer, and will be replaced if the deposit becomes depleted or nonviable during that period. Samples of the deposited strains will become available to the public and all restrictions imposed on access to the deposits will be removed upon grant of a patent on this application.

The present invention also provides methods for immunizing a subject against disease caused by infection by RSV comprising administering to the subject an immunoeffective amount of an attenuated RSV and in particular, cold-adapted and/or temperature sensitive RSV. Methods of making and using such attenuated RSV in a pharmaceutical composition e.g., a vaccine, are also provided.

Additional objects, advantages, and features of the present invention will become apparent from the following description, drawings and appended claims.

BRIEF DESCRIPTION OF THE DRAWINGS

The various advantages of the present invention will become apparent to one skilled in the art by reading the following specification and subjoined claims and by referencing the following drawings in which:

FIG. 2A is a graph showing the anti-RSV-F antibody titers (after 4 weeks) of mice immunized with an immunogenic composition of an aspect of the present invention;

FIG. 2B is a graph showing the anti-RSV-F antibody titers (after 8 weeks) of mice immunized with an immunogenic composition of an aspect of the present invention;

FIG. 5 is a graph showing CTL activity of mice immunized with immunogenic compositions of aspects of the present invention.

DETAILED DESCRIPTION OF THE INVENTION

Figure 1A:
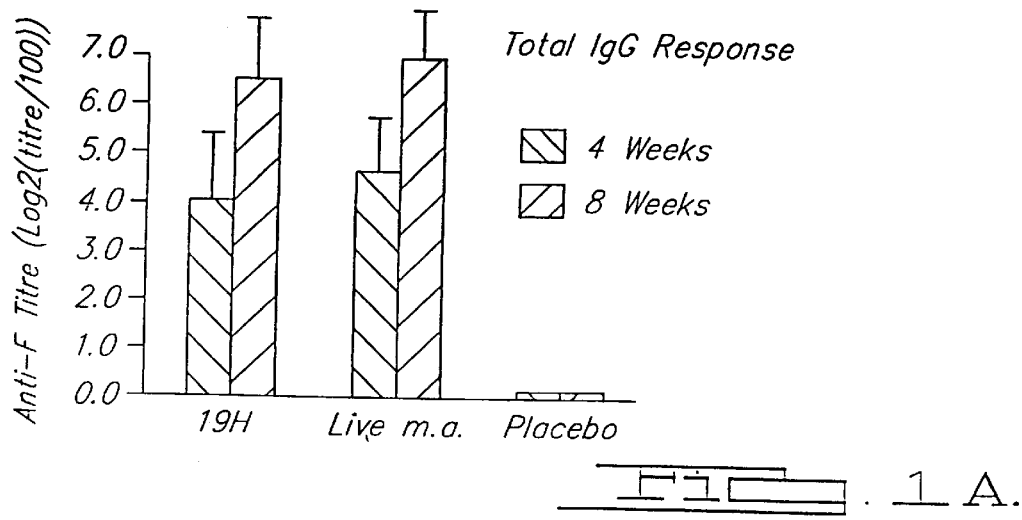
FIG. 1A is a graph showing the total anti-F IgG response of mice immunized with an immunogenic composition of an aspect of the present invention.
Figure 1B:
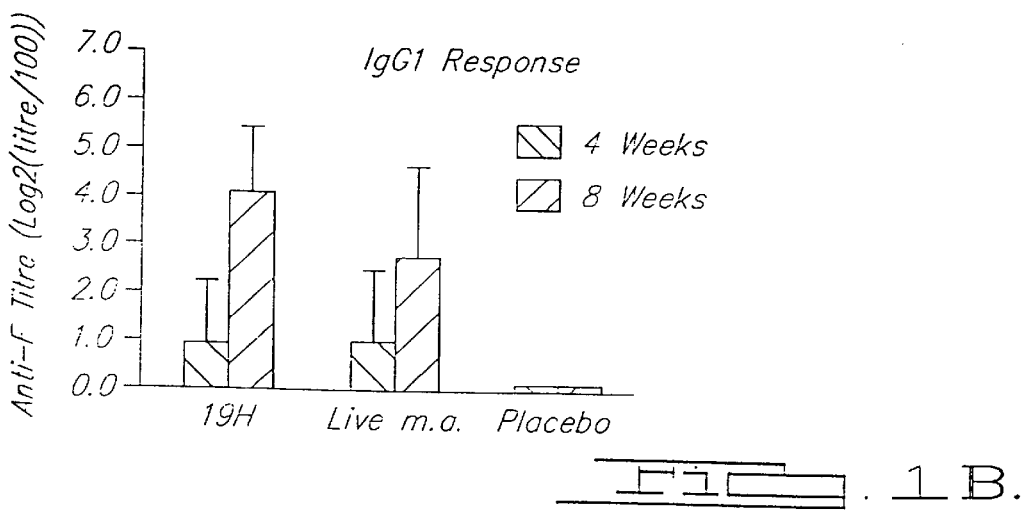
FIG. 1B is a graph showing the anti-F $IgG_1$ response of mice immunized with an immunogenic composition of an aspect of the present invention.
Figure 1C:
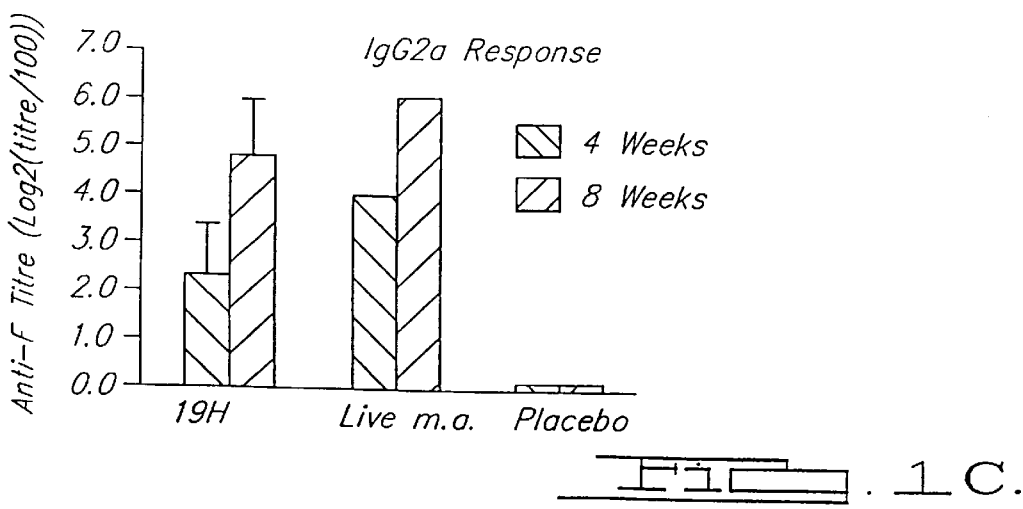
FIG. 1C is a graph showing the anti-F $IgG_{2a}$ response of mice immunized with an immunogenic composition of an aspect of the present invention.

Attenuated RSV including cold-adapted and/or temperature sensitive RSV, as well as progenitor viruses, are provided and have been deposited with the ATCC and are described in detail herein. As used herein, the term "cold-adapted" means a virus that has been attenuated by propagation at lower than optimal growth temperatures and the term "temperature sensitive" means that replication of the virus is impeded as temperature is elevated.

The lines of the present invention have been successfully attenuated using three different approaches: adaption to suboptimal temperature by direct and stepwise passage; high passages at 35° C.; and, adaption to a heterologous host (i.e., host-range restricted). Four of the deposited lines have also been plaque purified (19HL 3PI, 19H 3PI, 19H MD and CRIa MD). The attenuated RSV of the present invention are genetically-stable, immunogenic and protective, and avirulent, and are thus particularly useful in the formulation of live, attenuated RSV vaccines which are capable of eliciting a protective immune response without causing unacceptable symptoms of severe respiratory disease. The immune response which is achieved in the subject by the method of an embodiment of the present invention preferably includes the production of virus specific neutralizing antibodies and the virus specific cytotoxic T-cell responses. The invention is therefore particularly effective to provide protection against respiratory tract diseases caused by RSV.

Methods of attenuating RSV, for example, attenuating the deposited progenitor viruses, as well as methods of making and using attenuated RSV vaccines, are also provided by the present invention, including the preparation of pharmaceutical compositions.

Nucleic acid molecules encoding the attenuated RSV are also within the scope of the present invention. These nucleic acids may be DNA molecules, cDNA molecules or RNA molecules e.g., antisense RNA. The present invention further includes nucleic acid molecules which differ from that of the nucleic acid molecules which encode the RSV of the present invention, but which produce the same cold-adapted and temperature sensitive phenotypic effect. These altered, phenotypically equivalent nucleic acid molecules are referred to as "equivalent nucleic acids." The present invention also encompasses nucleic acid molecules characterized by changes in non-coding regions that do not alter the phenotype of the polypeptide produced therefrom, when compared to the nucleic acid molecules of the RSV described herein.

Also encompassed by the present invention are the nucleic acid molecules comprising noncoding sequences of the RSV of the present invention. These non-coding regions are to include 5' noncoding regions, 3' noncoding regions, intergenic sequences, and other noncoding regions of the viral genome. These include, but are not limited to, transcriptional, translational and other regulatory regions. These nucleic acid molecules also may be DNA molecules, cDNA molecules or RNA molecules.

Nucleic acid molecules which hybridize under stringent conditions to the nucleic acid molecules described herein are also within the scope of the present invention. As will be appreciated by those skilled in the art, multiple factors are considered in determining the stringency of hybridization including species of nucleic acid, length of nucleic acid probe, $T_m$ (melting temperature), temperature of hybridization and washes, salt concentration in the hybridization and wash buffers, aqueous or formamide hybridization buffer, and length of time for hybridization and for washes. An example of stringent conditions are DNA—DNA hybridization with a probe greater than 200 nucleotides in 5× SSC, at 65° C. in aqueous solution or 42° C. in formamide, followed by washing with 0.1× SSC, at 65° C. in aqueous solution. (Other experimental conditions for controlling stringency are described in Maniatis, T. et al., *Molecular Cloning: a Laboratory Manual*, Cold Springs Harbor Laboratory, Cold Springs, N.Y. (1982) at pages 387–389 and Sambrook, J. et al., *Molecular Cloning: a Laboratory Manual*, Second Edition, Volume 2, Cold Springs Harbor Laboratory, Cold Springs, N.Y., at pages 8.46–8.47 (1989)).

The nucleic acid molecules of the present invention may be operatively-linked to a promoter of RNA transcription, as well as other regulatory sequences. As used herein, the term "operatively-linked" means positioned in such a manner that the promoter and other regulatory sequences will direct the transcription off of the nucleic acid molecule. An example of a promoter is the T7 promoter. Vectors which contain both a promoter and a cloning site to which an inserted piece of nucleic acid is operatively-linked to the promoter, are well known in the art. Preferably, these vectors are capable of transcribing nucleic acid in vitro and in vivo.

Purified polypeptides isolated from the RSV described herein or from cells infected with these same virus, are also encompassed by the present invention. The polypeptides (or fragments thereof) may be of varying length, and preferably will be capable of exhibiting immunological activity.

Methods for producing polypeptides of the present invention are also within the scope of the present invention. In one embodiment, RSV polypeptides can be isolated in substantially pure form from RSV or cultures of cells infected with RSV. In an alternative embodiment, RSV polypeptides can be isolated from a recombinant system or are vector-engineered to produce these polypeptides. In yet another embodiment, RSV polypeptides can be chemically synthesized by methods well known to those of skill in the art.

All derived RSV strains including the deposited attenuated RSV derived from the progenitor viruses, are also encompassed by the present invention, including, without limitation, those attenuated by cold adaptation (including both direct and stepwise passage), high in vitro passage, host-range restriction and chemical or genetic modification e.g., site-directed mutagenesis.

Although the deposited RSV of the present invention are subgroup A virus, it will be appreciated by those skilled in the art that subgroup B virus can be produced by biologically cloning wild-type subgroup B virus in an acceptable cell substrate using methods known in the art. The subgroup B virus may then be attenuated as described herein.

Pharmaceutical compositions comprising any of the RSV described herein or polypeptides, either alone or in combination, and a pharmaceutically acceptable carrier, are also provided by the present invention. As used herein, the phrase "pharmaceutically acceptable carrier" encompasses any of the standard pharmaceutical carriers, such as physiologically balanced culture medium, phosphate buffered saline solution, water, and emulsions, such as an oil/water emulsion, various types of wetting agents and protein stabilizers. Each carrier must be "acceptable" in the sense of being compatible with the other ingredients of the formulation and not injurious to the patient. Formulations include those suitable for oral, nasal, topical (including transdermal, buccal and sublingual), parenteral (including subcutaneous) and pulmonary administration. The pharmaceutical compositions may conveniently be presented in unit dosage form and may be prepared by any method known in the art.

In one embodiment of the present invention, the pharmaceutical composition is intended for use as a vaccine. In such embodiment, a virus may be mixed with cryoprotective additives or stabilizers such as proteins (e.g., albumin, gelatin), sugars (e.g., sucrose, lactose, sorbitol), amino acids (e.g., sodium glutamate), saline, or other protective agents. This mixture may then be desiccated or lyophilized for transport and storage, and reconstituted prior to administration. Lyophilized virus will typically be maintained at about 4° C. and when ready for use, reconstituted in a stabilizing solution, with or without adjuvant. In yet another embodiment of the present invention, the virus may be inactivated and may be mixed with an adjuvant, saline and a detergent such as phosphate Tween buffer. For further methods of vaccine preparation, see Duffy, J. I., *Vaccine Preparation Techniques*, Noyes Data Corporation, (1980).

Immunogenicity can be significantly improved if the virus is co-administered with an immunostimulatory agent or adjuvant. Adjuvants enhance immunogenicity but are not necessarily immunogenic themselves. Immunostimulatory agents or adjuvants have been used for many years to improve the host immune responses to, for example, vaccines.

Suitable adjuvants are well known to those skilled in the art and include, without limitation, aluminum phosphate, aluminum hydroxide, QS21, Quil A, derivatives and components thereof, calcium phosphate, calcium hydroxide, zinc hydroxide, a glycolipid analog, an octodecyl ester of an amino acid, a muramyl dipeptide, polyphosphazene, a lipoprotein, ISCOM matrix, DC-Chol, DDA, and other adjuvants and bacterial toxins, components and derivatives thereof.

Pharmaceutical compositions comprising any of the attenuated RSV of the present invention are useful to immunize a subject against disease caused by RSV infection. Thus, this invention further provides methods of immunizing a subject against disease caused by RSV infection, comprising administering to the subject an immunoeffective amount of a pharmaceutical composition of the invention. This subject may be an animal, for example a mammal, such as a primate or preferably a human.

The vaccines are administered in a manner compatible with the dosage formulation, and in such amount as will be therapeutically effective, immunogenic and protective. The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner and may be monitored on a patient-by-patient basis. However, suitable dosage ranges are readily determinable by one skilled in the art and generally range from about $10^2$ to about $10^9$ plaque forming units (PFU) or more of virus per patient, more commonly, from about $10^4$ to about $10^5$ PFU of virus per patient. The dosage may also depend, without limitation, on the route of administration, the patient's state of health and weight, and the nature of the formulation.

It will be appreciated that administration of the vaccines of the present invention will be by procedures well established in the pharmaceutical arts, such as intranasally, parenterally, intravenously, orally, or topically applied to any mucosal surface such as intranasal, oral, eye or rectal surface. Moreover, as described in more detail in Specific Example 3E., more than one route of administration may be employed either simultaneously or sequentially (e.g., boosting). In a preferred embodiment of the present invention, live, attenuated viral vaccines are administered intranasally, orally, parenterally or applied to any mucosal surface (nasal, oral, eye, rectal). Inactivated whole virus vaccine is preferably administered parenterally or to any mucosal surface.

Upon inoculation with an attenuated RSV pharmaceutical composition as described herein, the immune system of the host responds to the vaccine by producing antibodies, both secretory and serum, specific for RSV proteins. As a result of the vaccination, the host becomes at least partially or completely immune to RSV infection, or resistant to developing moderate or severe RSV infection, particularly of the lower respiratory tract.

It will be appreciated that the attenuated RSV of the present invention can be combined with viruses of other subgroups or strains to achieve protection against multiple strains of RSV. Typically the viruses will be in an admixture and administered simultaneously, but may also be administered separately. Due to the phenomenon of cross-protection among certain strains of RSV, immunization with one strain may protect against several different strains of the same or different subgroup.

In some instances it may be desirable to combine the attenuated RSV vaccines of the present invention with vaccines which induce protective responses to other agents, particularly other childhood viruses. For example, the vaccine compositions of the present invention can be administered simultaneously, separately or sequentially with other vaccines such as parainfluenza virus vaccine, as described in Elements, et al., *J. Clin. Microbiol.* 29:1175–1185 (1991). Moreover, a multivalent preparation may be employed comprising for example, the attenuated RSV of the present invention (including subgroups A and B), parainfluenza virus type 1, 2 and 3 and influenza virus types A and B.

It will also be appreciated that single or multiple administrations of the vaccine compositions of the present invention may be carried out. In neonates and infants, multiple administration may be required to elicit sufficient levels of immunity. Administration should begin within the first month of life, and continue at intervals throughout childhood, such as at two months, six months, one year and two years, as necessary to maintain sufficient levels of protection against wild-type RSV disease. Similarly, adults who are particularly susceptible to repeated or serious RSV infection, such as, for example, health care workers, day care workers, elderly and individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection.

Those skilled in the art will further appreciate that the viruses of the present invention may be used in diagnostic applications. For example, a method of determining the presence of antibodies specifically reactive with an RSV of the present invention is provided. Such a method comprises the steps of contacting a sample with the RSV to produce complexes comprising the virus and any antibodies present in the sample specifically reactive therewith, and determining production of the complexes. A similar method of determining the presence of RSV is provided wherein the sample is contacted with an antibody specifically reactive with an RSV to produce complexes comprising the antibody and the virus present in the sample that is specifically reactive with the antibody, and determining production of the complexes.

The virus of the present invention are characterized by a level of attenuation such that they do not produce RSV disease in a host immunized therewith, evoke a protective immune response and do not lead to immunopotentiation or exacerbated disease. They lack transmissibility, are genetically stable and exhibit cold-adapted and temperature sensitive markers. They are immunogenically protective and induce protective levels of humoral and cell mediated immunity. In particular, a balanced anti-RSV F IgG1/IgG2a response is seen in hosts immunized with attenuated viruses of the present invention. They can be administered by the natural route i.e., intranasally. The RSV of the present invention may be tested in in vitro and in vivo models to demonstrate these characteristics. A variety of animal models have been described and are summarized in Meignier et al., eds., *Animal Models of Respiratory Syncytial Virus Infection*, Merieux Foundation Publication (1991). A cotton rat model of RSV infection is described in U.S. Pat. No. 4,800,078 and Prince et al., *Virus Res.* 3:193–206 (1985), and is believed to be predictive of attenuation and efficacy in humans. A primate model of RSV infection using a chimpanzee is also useful in examining attenuation and protection and is described in detail in Richardson et al., *J. Med. Virol.* 3:91–100 (1978) and Wright et al., *Infect. Immun.* 37:397–400 (1982).

SPECIFIC EXAMPLES

The following Specific Examples illustrate practice of the invention. These examples are for illustrative purposes only and are not intended in any way to limit the scope of the claimed invention.

Specific Example 1 describes the production and characterization of the virus of the present invention including the passage status and procedures for developing the strains.

Specific Example 2 describes temperature sensitivity studies, wherein the deposited strains were found to have the ts phenotype (see Tables 2 and 3).

Specific Example 3 describes immunogenicity studies wherein mice were immunized by administering an RSV strain of the present invention. As described in Specific Examples 3A–3D., mice were immunized and sera examined four weeks after boosting for anti-F, total IgG antibodies, IgG1 and IgG2a antibodies. The results are shown in FIGS. 1A–3 and Tables 4–7 and show that the intranasal immunization with the attenuated RSV produces a substantial anti-F antibody response. In particular, a balanced anti-RSV F IgG1/IgG2a response demonstrating the induction of both Th-1 and Th-2 type responses was achieved. The generation of IgG2A antibodies in the murine model is indicative of a Th1-type immune response. The level of virus-neutralizing antibodies was also determined, by plaque reduction assays.

In Specific Example 3E., a study was performed to evaluate the effect of boosting by a route of administration that differs from the initial inoculation route of administration. In particular, mice were inoculated intranasally and boosted in the footpad and intramuscularly. Neutralization titer data is set forth in Table 8.

Figure 4:
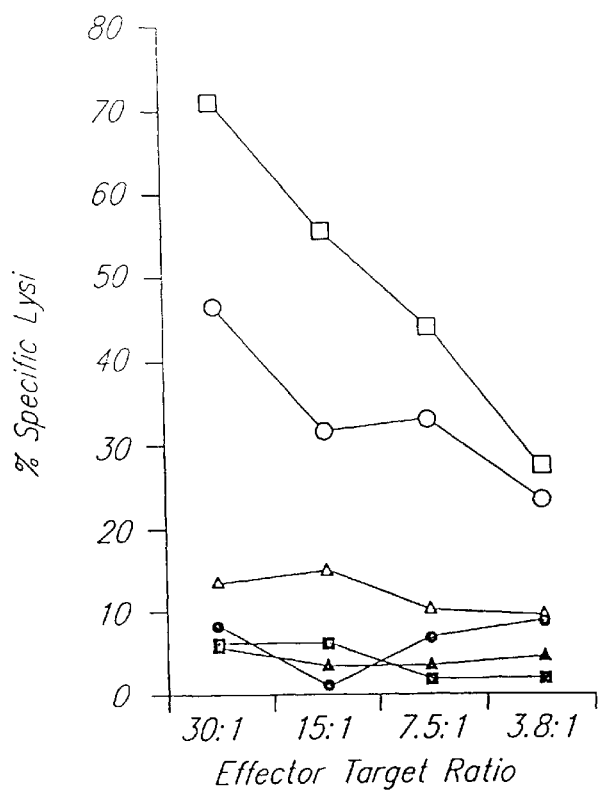
FIG. 4 is a graph showing cytotoxic T cell (CTL) activity of mice immunized with an immunogenic composition of an aspect of the present invention.

As described in Specific Examples 3F. and 3G., the generation of RSV-specific cytotoxic T cells (CTL) following immunization was determined and the results shown in FIGS. 4 and 5. Immunizing animals with the attenuated RSV of the present invention induced significant levels of CTL activity. In addition, as shown in Table 9, mice immunized with the plaque purified viruses of the present invention were protected against live virus challenge.

Specific Example 4 describes sequence analysis of the F gene of several RSV lines. Specific Example 4A. sets forth the comparison of the sequences for wild type RSV (referred to herein as WRSV) and two attenuated lines, Ca19V and 19H (see Table 10). Specific Example 4B. illustrates the comparison of the sequences for the line 19 progenitor strain (referred to herein as wt 19) and the same two lines, lines Ca19V and 19H (see Table 11). The F genes of the two attenuated lines both differ from the WRSV as well as the wt 19, but have 66 nucleotides and 11 amino acids in common. With respect to the amino acid differences between the attenuated lines and the wt 19, none of the amino acid differences are shared by the two attenuated lines.

Specific Example 5 describes the plaque purification of the attenuated RSV lines of the present invention. Table 12 illustrates the temperature sensitivity of the plaque purified lines.

Specific Example 6 describes RSV therapeutic protocols for administering the pharmaceutical compositions of the present invention to humans.

Specific Example 1

Production and Characterization of Virus

A. The following sets forth the deposited RSV strains and their titers.

1. 19H
    in EMEM 5% FBS 5% Glycerol
    $1.00 \times 10^8$ $TCID_{50}$ in MRC Tubes on Day 14
    $1.85 \times 10^5$ Pfu's/ml in VERO cells
    ATCC Designation No. VR-2513
2. Ca19S
    in EMEM 5% FBS 5% Glycerol
    $7.00 \times 10^4$ Pfu's/ml in VERO cells
    ATCC Designation No. VR-2512
3. Ca19V
    in 199 5% FBS 5% Glycerol
    $1.00 \times 10^7$ Pfu's/ml in VERO cells
    ATCC Designation No. VR-2515
4. Ca48V
    in 199 5% FBS 5% Glycerol
    $9.00 \times 10^4$ Pfu's/ml in VERO cells
    ATCC Designation No. VR-2514
5. CaBCV
    in 199 5% FBS 5% Glycerol
    $1.30 \times 10^4$ Pfu's/ml in VERO cells
    ATCC Designation No. VR-2516
6. CRIa
    in 100 5% FBS 5% Glycerol
    $6.00 \times 10^3$ Pfu's/ml in VERO cells
    ATCC Designation No. VR-2511
7. CaBCL
    in 199 5% FBS 5% Glycerol
    $1.70 \times 10^4$ in VERO cells
    ATCC Designation No. VR-2517
8. 19H 4MD
    in 5% Glycerol
    $3.2 \times 10^5$ $TCID_{50}$/ml in MRC5 cells
    ATCC Designation No. VR-2567.
9. 19H 3PI
    in 5% Glycerol
    $4 \times 10^5$ $TCID_{50}$/ml in MRC5 cells ATCC Designation No. VR-2564.

10. 19H 5MD
   in 5% Glycerol
   $3.2 \times 10^5$ TCID$_{50}$/ml in MRC5 cells
   ATCC Designation No. VR-2565.

11. CRIa MD
   in 5% Glycerol
   $4 \times 10^5$ TCID$_{50}$/ml in MRC5 cells
   ATCC Designation No. VR-2566.

12. 19HL 3PI
   in 5% Glycerol
   $2.0 \times 10^6$ TCID$_{50}$/ml in MRC5 cells
   ATCC Designation No. VR-2572.

13. wt 19
   in 5% Glycerol
   $3.0 \times 10^5$ TCID$_{50}$/ml in MRC5 cells
   ATCC Designation No. VR-2570.

14. WRSV
   in 5% Glycerol
   $2.0 \times 10^5$ TCID$_{50}$/ml in MRC5 cells
   ATCC Designation No. VR-2571.

B. The following depicts the passage status of exemplary derivative RSV strains of the present invention.

1. Line 19 MRC5 72–35°
2. Line 19 MRC5 24–25° st 1–33°
3. Line 19 MRC5 10–25° VERO 16–25° 6–20°3–33°
4. Line 48 MRC 14–25° st 1–33° VERO 10–25° 1–33°
5. CRSV-BC5 CL17 MRC 30–25°
6. Ia-CRSV-5 CL15 MRC 27–25°
7. CRSV-BC13 MRC 19–25° 1–33°
8. Line 19 MRC5 P-70–35°, VERO P-3–35°, MRC5, P-2–35° clone 2 (3PI) plaque purified
9. Line 19 MRC5, P-92–35°, clone 5-1, purified by minimal limited dilution (MLD)
10. Ia-CRSV-5, MRC5, P-38–25°, MRC5, P-1–33°, purified by MLD
11. Line 19 HP clone 4-1, MRC5, P-103–33°, purified by MLD
12. Line 19 MRC 70–35° C., Vero P-35° C., large clone 6–35° (3PI), plaque purified C. The following are the procedures for developing the attenuated deposited RSV strains of the present invention (see Specific Example 5 for additional details regarding the plaque purification). CRIa, CRIa MD, CaBCL and CaBCV were derived from WRSV. 19H, Ca19S, Ca19V, 19H 4MD, 19H 3PI, 19H 5MD and 19HL 3PI were derived from wt 19.

1. 19H

MRC5 cells were purchased in tubes from Bio Whittaker Laboratories. Media was removed. 1.2 ml EMEM +5% FBS was added to each tube. 0.3 ml virus was added to each of 4 tubes. Tubes were incubated at 35° C. and observed for development of cytopathic effect (CPE). Tubes were frozen at −70° C. Virus was harvested and passed to fresh cells.

2. Ca19S

The same steps as in 1. above were performed, except that tubes were passed 10 times at 35° C.; 10 times at 30° C.; 15 times at 25° C., and 2 times at 33° C.

3. Ca19V

The first 10 passages in MRC5 cells were performed as described in 1. above except that tubes were incubated at 25° C. Media was removed from 3 confluent 25 cm$^2$ VERO flasks. Virus was diluted 1:5 in 1×199+5% FBS. 1 ml of virus was added to each of 2 flasks (1 flask is used as a control). Virus was adsorbed on a rocker at room temperature for 2 hours. 4 ml of 1×100+5% FBS was added to each flask. Flasks were incubated at the appropriate temperature until 80% CPE was observed. Flasks were frozen at −70° C. Virus was harvested and passed to fresh cells. Virus was passed 16 times at 25° C.; 6 times at 20° C.; and, 2 times at 33° C.

4. Ca48V

The first 14 passages in MRC5 cells were performed as described in 2. above. Passage in VERO cells was performed as in 3. above. Virus was passed 10 times in VERO cells at 25° C. and 1 time at 33° C.

5. CaBCV, CRIa and CaBCL

Same as 2. above except that 199+5% FBS was used.

An efficient plaque purification system was used (where indicated), which can evaluate individual plaques for temperature sensitivity. The following procedures were employed. Monolayers of Vero cells grown in 6- or 12-well plates were infected with 10-fold serial dilutions of virus in EMEM medium supplemented with 5% FBS and L glutamin. Each dilution was plated into three replicate wells. Virus was absorbed by incubation at 35° C. on a rocker for 2 hours. The inoculum was removed and the cells were overlaid with 0.6% (WN) Sea Kem ME agarose (final concentration) and 1×EMEM 3.5% FBS, L glutamine and gentamycin. The plates were allowed to solidify at room temperature and were incubated in $CO_2$ in parallel at 25° C., 33° C., 37° C. and 39° C. for 4 days. To clearly visualize developing plaques, a second overlay of agarose medium containing the same first overlay agarose medium with additional 0.01% (WN) neutral red, was added on the fourth date after infection and plates were incubated in $CO_2$ at the appropriate temperature. Individual plaques were picked and were emulsified in 0.5 ml EMEM 5% FBS and either amplified or frozen at −70° C.

Each virus was evaluated by the time of plaque appearance, the plaque morphology, size and its characterization and titer. The growth of a given virus was expressed as (PFU/ml) for titration. The picked plaques were used to inoculate duplicate tubes containing Vero cell monolayers. One duplicate was incubated at 33° C. and the other at 39° C. up to 14 days. Cultures were checked for virus CPE. The tubes which demonstrated easily detectable CPE at 33° C., and no CPE at 39° C. were selected for further plaque purification, titration and temperature sensitivity studies.

Conventional minimal limited dilution procedures, known to those skilled in the art, were followed where indicated.

Specific Example 2

Temperature Sensitivity Studies

To screen the cold-adapted and high passage virus for the presence of temperature sensitive (ts) variants, viruses were tested at 39° C., 37° C. and 33° C. by one of two methods of titration: plaque immunoassay or TCID$_{50}$.

Results

Line 19H is ts when assayed in both MRC cells and under agarose in Vero cells. Line Cal 9S has a 5 log reduction in growth at 39° C. versus that at 33° C. Line CRIa is also ts in MRC cells. WRSV grows as well at 39° C. as it does at 33° C.

Lines Cal 9V and Ca48V are both ts when assayed in Vero cells using the second antibody technique and under agarose. Line Cal 9V has a 5 log reduction in growth at 39° C. versus that at 33° C. and line Ca48V has a 3 log reduction in growth at the non-permissive temperature.

The following tables further set forth the results of the temperature sensitivity study.

TABLE 2

$TCID_{50}$ in MRC Cells on Day 14

| Virus Lines | 33° C. | 37° C. | 38° C. | 39° C. |
|---|---|---|---|---|
| 19H | $1.00 \times 10^8$ | | | $3.16 \times 10^5$ |
| 19H | $4.68 \times 10^6$ | $2.15 \times 10^5$ | | $4.68 \times 10^4$ |
| Ca19S | $3.16 \times 10^7$ | | $3.16 \times 10^3$ | $3.16 \times 10^2$ |
| CRIa | $4.68 \times 10^3$ | | $4.68 \times 10^2$ | $3.16 \times 10^1$ |
| WRSV | $3.16 \times 10^4$ | | $3.16 \times 10^4$ | $1.00 \times 10^4$ |

TABLE 3

Pfu's in Vero Cells on Day 7

| Virus Lines | 33° C. | 37° C. | 38° C. | 39° C. |
|---|---|---|---|---|
| Ca19V | $3.16 \times 10^{10}$ | | $5.85 \times 10^9$ | $2.54 \times 10^5$ pinpoint plaques |
| Ca48V | $2.50 \times 10^7$ | $8.00 \times 10^6$ | | $6.00 \times 10^4$ pinpoint plaques |

Materials and Methods $TCID_{50}$ in MRC5 Cells. Virus to be titrated was diluted $10^{-1}$ in EMEM +5% FBS. Confluent MRC5 tubes were used, for each dilution and for each temperature (total of 96 tubes for 3 temperatures). 1 ml of a viral dilution was added to each ube. Tubes were incubated at 33° C., 37° C. or 38° C., and 39° C. Tubes were read daily to day 14 for CPE. $TCID_{50}$ was calculated using the method of Reed and Muench.

Plaque Immunoassay—Pfu's in HEP2 Cells or Vero Cells. HEP2 Cells (or VERO cells) were grown in a 12 well microtiter plate until semi-confluent and media was removed. Virus was diluted in 1×199+5% FBS $10^{-1}$ to $10^{-7}$. Cells were inoculated in triplicate, 0.5 ml/well and allowed to adsorb at 35° C. for 2 hours. Inoculum was then removed. The cells were overlaid with 2 ml of the 1:1 mixture of 2× EMEM with 6% FBS and the 4% Methyl Cellulose (4 gm Methyl Cellulose and 100 ml Type I Deionized Water, autoclaved to sterilize; final concentration 2% Methyl Cellulose) and incubated at 35° C. with 5% $CO_2$ for 7 days. Overlay media was then discarded. The cells were fixed with cold 80% methanol at −70° C. for 1 hour. The methanol was then removed and the plates were frozen at −70° C. Plates were allowed to thaw at room temperature. 1 ml of 5% Blotto media (25 gm Milk and 500 ml PBS) was added to each well and the wells were incubated at 35° C. for 30 minutes. 5% Blotto media was then removed and 1 ml of 5% Blotto media with 1/100 dilution of anti-RSV antibody was added. Incubation at 35° C. for 30 minutes took place. After incubation, 5% Blotto media with antibody was removed and cells were washed with 5% Blotto media. 1 ml of 5% Blotto media with 1/100 dilution of conjugate antibody was then added and incubation took place at 35° C. for 30 minutes. 5% Blotto media with conjugate antibody was removed and cells were washed with PBS. 1 ml of 1:1 mix of peroxide solution substrate (4 chloro-1 napthol)+$H_2O_2$ was added and incubation took place at room temperature for 1–5 minutes. During this period color development was watched carefully. Cells were then washed with PBS. Plaques were counted and Pfu's recorded.

Specific Example 3

Immunogenicity Studies

A. Immunogenicity of RSV Lines (Study 1)

A study was performed to determine the immunogenicity of line 19H. Pathogen-free BALB/c mice (approximately 8 weeks old) were immunized intranasally with either $1.6 \times 10^6$ $TCID_{50}$ of 19H, $2.5 \times 10^5$ pfu of A2 mouse adapted virus (designated live virus), or 5% glycerol (designated placebo). Animals were bled 4 weeks after the primary inoculation and boosted at 4 weeks with an equivalent dose of the vaccine formulation. Serum samples were also taken 4 weeks after the booster dose. Anti-F antibody titer was determined as follows: immunoaffinity purified RSV-F antigen was coated on wells of Nunc-immuno Maxi Sorp flat bottom microtiter plates, by incubating antigen overnight at room temperature in 0.05M Carbonate—Bicarbonate buffer, pH 9.6. Wells were blocked for non-specific binding by adding 0.1% BSA in PBS for 30 min. at room temperature, followed by two washes in a washing buffer of 0.1% BSA in PBS +0.1% Tween 20. Mice sera was diluted in two or four-fold serial dilutions, and added to wells. After 1 hour incubation at room temperature, plates were washed five times with washing buffer, and horseradish peroxidase labeled conjugate was added at the appropriate optimal dilution in washing buffer. The total IgG assay used $F(ab')_2$, goat anti-mouse IgG (H+L specific)-HRP from Jackson Immuno Research Laboratory Inc., Baltimore. The IgG 1 assay used sheep anti-mouse IgG1-HRP from Serotec. The IgG 2a and IgA assays used goat anti-mouse IgG 2a-HRP and goat-anti-mouse IgA-HRP respectively, from Caltag Laboratories, San Francisco. Following 1 hour incubation at room temperature, the plates were washed five times with washing buffer, and a substrate hydrogen peroxide in the presence of tetramethylbenzidine was added. The color reaction was stopped by adding 2M sulfuric acid. The color was read in a Multiscan Titertek plate reader at an optical density (OD) of 450 nm. The titre was taken as the reciprocal of the last dilution at which the OD was approximately double. This OD must be greater than the negative control of the assay at the starting dilution. The pre-immune serum of each animal was used as the negative control.

Line 19H elicited levels of anti-F IgG antibodies that were equivalent to those induced by the A2 mouse adapted virus (see FIGS. 1A, 1B and 1C). Sera from animals that received two doses of line 19H had a balanced anti-RSV F $Ig_1/IgG_{2a}$ response. As outlined in the table below, the sera of animals that were immunized with two doses of 19H had RSV-specific neutralizing antibodies that were comparable to those obtained following inoculation with live mouse adapted RSV. hus, line 19H was immunogenic in the mouse model.

TABLE 4

| Serum antibody response of BALB/c mice immunized with ts mutant | | |
|---|---|---|
| | Neutralization titer[a,b] ($log_2$ ± s.d.) | |
| Formulation | 4 Week Bleed | 8 Week Bleed |
| 19H | 8.2 ± 0.9 | 9.5 ± 1.2 |
| Live RSV (mouse- | 8.5 ± 0.8 | 10.6 ± 0.7 |

TABLE 4-continued

Serum antibody response of BALB/c mice immunized with ts mutant

| | Neutralization titer[a,b] | |
|---|---|---|
| | (log$_2$ ± s.d.) | |
| Formulation | 4 Week Bleed | 8 Week Bleed |
| adapted A2 virus) | | |
| Placebo | <3.3 ± 0.0 | <3.3 ± 0.0 |

[a]Neutralization titer determined by complement-enhanced 60% plaque-reduction assay
[b]Each value represents the reciprocal mean titer of at least 6 animals

B. Immunogenicity of RSV Lines (Study 2)

A second study was performed to determine the immunogenicity of the following RSV lines: WRSV (Vero 35°$_1$, titer 2.00×10$^6$ Pfu's/ml in Vero cells), CRIa, CaBCV, 19H, Ca19V and Ca48V. Balb/c/AnNTacfBR three week old male mice from Taconic, 272 Hoover Avenue, Germantown, NY 12526, were used. Mice were anesthetized IP with 200 µl ketoset diluted 1:10 and inoculated IN with 50 µl undiluted virus, 6 mice/group. Mice were boosted with 50 µl virus diluted 1:2 in 199 media. Approximately one week later, mice were bled for serum. Neutralization titers were done in VERO cells.

All of the lines tested for neutralization antibodies had titers of at least 1:20. Line 19H had a titer of 1:80, however, WRSV had a titer of 1:320. The following tables further set forth the results of the immunogenicity study.

TABLE 5

| Neutralization Titers (60% Reduction) without Complement[†] | |
|---|---|
| Antiserum to Virus | Titers |
| 19H | 1:80 |
| CRIa | 1:40 |
| Ca19V | 1:20 |
| CaBCV | 1:40 |
| Ca48V | 1:40 |
| WRSV | >1:320 |
| Normal Serum | <1:20 |

[†]Serum periodate and heat treated (56° for 1 hour); serum diluted in presence of 2.5% FBS.

TABLE 6

| ELISA Titers* | |
|---|---|
| Antiserum to Virus | Titers[+] |
| 19H | 1:1280 |
| CRIa | 1:320 |
| Ca19V | 1:1280 |
| CaBCV | 1:2560 |
| Ca48V | neg |
| WRSV | 1:640 |

*Antigen-Whole RSV Virus
[+]Titers corrected for normal serum

C. Immunogenicity Of RSV Lines (Study 3)

A third study was performed to determine the immunogenicity of the following RSV lines: Ca19S, 19H, Ca19V, Ca48V, WRSV and Line 19 MRC5 28 25° (not deposited). Mice were infected with wild type and the RSV lines with twice boosted procedures, similar to the procedure described above. As shown in the table below, serum neutralization titers, carried out in the presence of complement, were reported as the reciprocal of the last dilution which reduced the number of viral plaques by 60%. Also shown in the table below, ELISA titers were reported as the reciprocal of the last dilution which had an OD reading of 0.1 or greater after correction for normal serum. All the lines tested for neutralization antibodies had titers of at least 320 and ELISA titers ranging from 160 to 40,960 after the second boost. Although line Ca19S produced the highest neutralization titer, all lines were similar in neutralizing ability and reached peak titer after the first boost. Line Cal 9V produced the highest ELISA IgG titer. All RSV attenuated lines were immunogenic.

TABLE 7

| Neutralization and ELISA Titers of Mice Immunized with Vaccine Lines | | | | | | | |
|---|---|---|---|---|---|---|---|
| | | Neutralization[b] | | | ELISA IgG[c] | | |
| Viruses[a] | Titers OF Inoculum | 2 Weeks[d] | 4 Weeks | 6 Weeks | 2 Weeks | 4 Weeks | 6 Weeks |
| WRSV | 5.3 | 80 | 640 | 320 | 160 | 2560 | 80 |
| Line 19 MRC5 28 25° | 5.7 | 80 | 640 | 1280 | 160 | 640 | 1280 |
| Ca19S | 7.5 | 80 | 640 | 640 | 320 | 2560 | 1280 |
| 19H | 7.3 | 80 | 320 | 320 | 80 | 2560 | 320 |

TABLE 7-continued Neutralization and ELISA Titers of Mice Immunized with Vaccine Lines

| Viruses[a] | Titers OF Inoculum | Neutralization[b] | | | ELISA IgG[c] | | |
|---|---|---|---|---|---|---|---|
| | | 2 Weeks[d] | 4 Weeks | 6 Weeks | 2 Weeks | 4 Weeks | 6 Weeks |
| Ca19V | 6.3 | 320 | 640 | 640 | 320 | 5120 | 40960 |
| Ca48V | 7.4 | 80 | 320 | 320 | 160 | 5120 | 10240 |

[a]Viruses used were not plaque purified.
[b]Reported as reciprocal of last dilution which reduced viral plaques by 60%.
[c]Reported as reciprocal of last dilution which had an OD of 0.1 or greater after adjustment for normal serum.
[d]Weeks after Initial Vaccination.

D. Immunogenicity Of RSV Lines (Study 4)

Figure 3B:
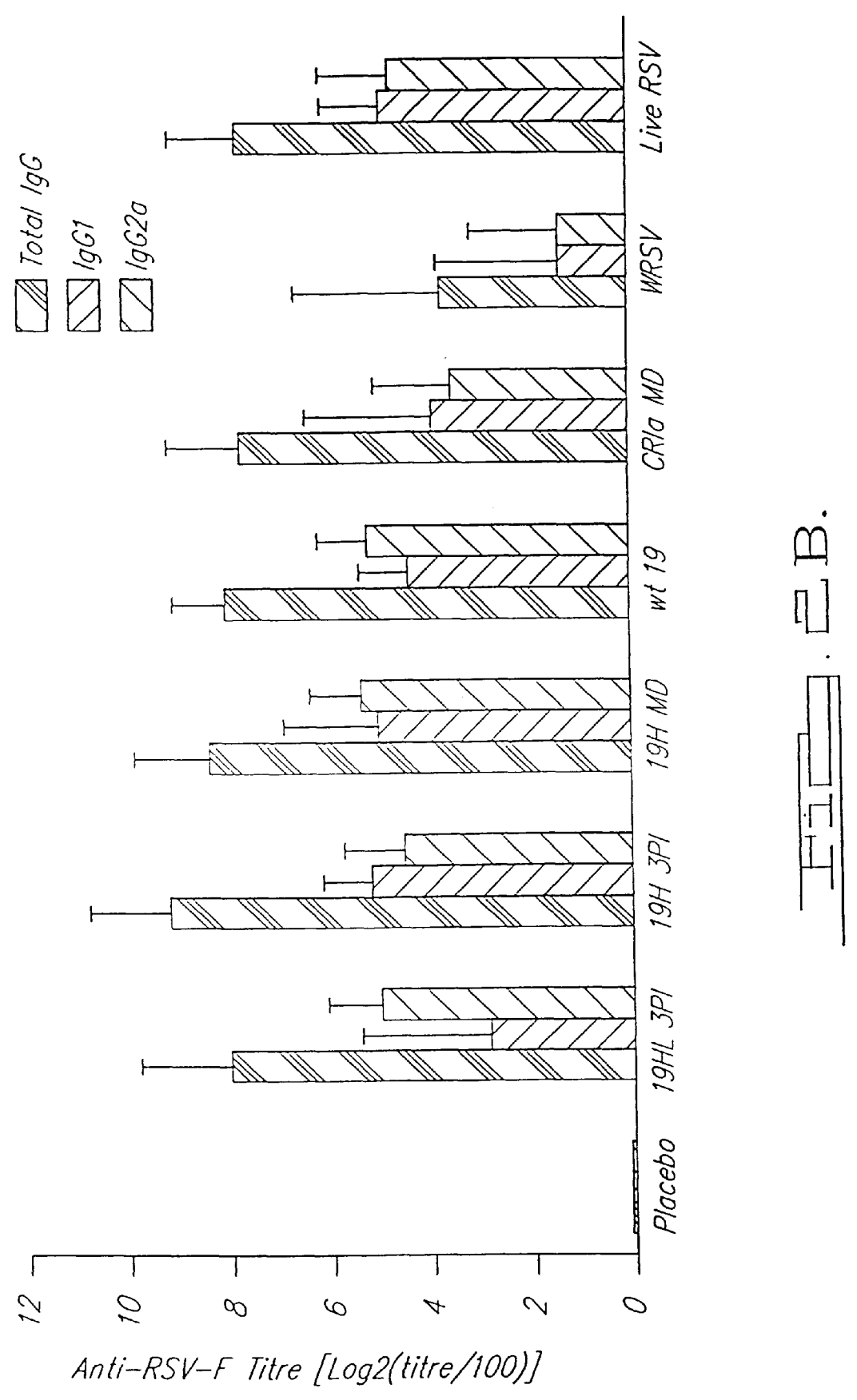
Figure 3:
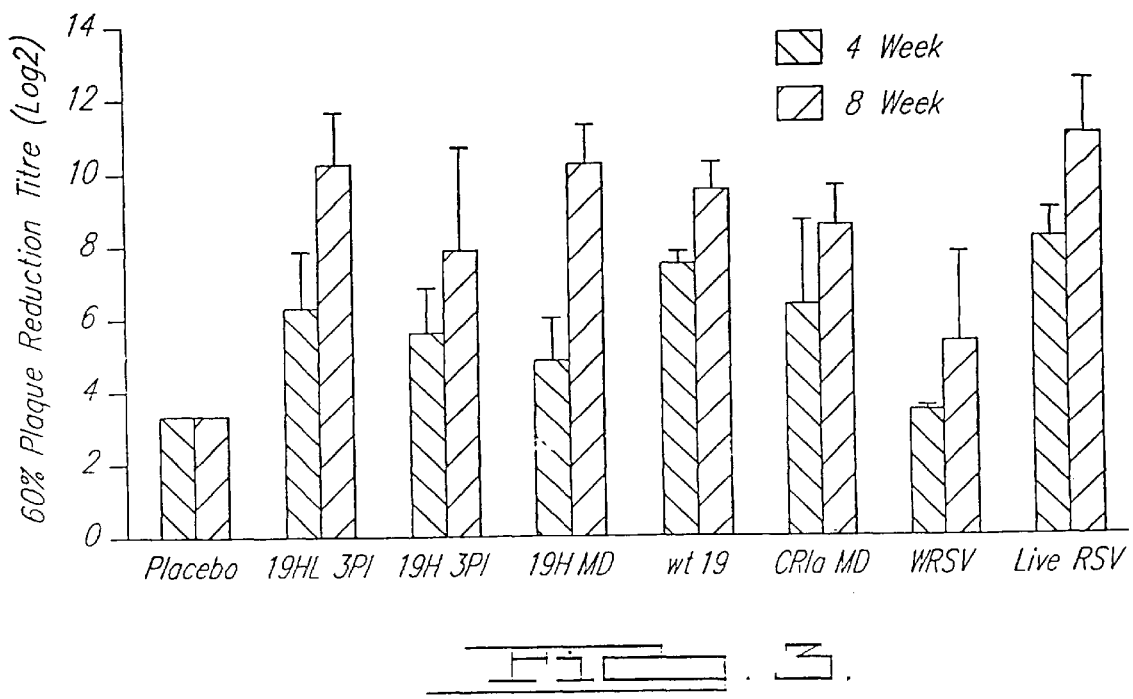
FIG. 3 is a graph showing RSV specific neutralizing antibody titers (after 4 and 8 weeks) of mice immunized with an immunogenic composition of an aspect of the present invention.

A fourth study was performed to determine the immunogenicity of the following plaque purified RSV lines: 19HL 3PI, 19H 3PI, 19H MD and CRIa MD. Pathogen-free BALB/c mice (approximately 8 weeks old) were immunized intranasally with either $2 \times 10^4$ TCID50 of the lines or their respective progenitor viruses (designated wt 19 and WRSV), $2.0 \times 10^4$ pfu of mouse-adapted virus (designated live virus), or medium +5% FBS +5% glycerol (designated placebo). Animals were bled 4 weeks after the primary inoculation and boosted at 4 weeks with an equivalent dose of the vaccine formulation. Serum samples were also taken 4 weeks after the booster dose. All plaque purified lines elicited anti-F IgG antibodies at 4 and 8 weeks (see FIGS. 2A and 2B, wherein each value represents the mean titer of antisera from 6 animals). At the 8 week time point, the sera of animals that had received 2 doses of the various plaque purified lines had anti-RSV F IgG antibody titres that were comparable to that observed in the sera of mice that were immunized with the mouse-adapted virus (designated live virus). As shown in FIG. 3 (values represent the mean titer of antisera from 6 animals), the sera of animals that were immunized with two doses of the various plaque purified lines had high levels of RSV-specific neutralizing antibodies. Thus, all RSV attenuated lines tested were immunogenic in the mouse model.

E. Boosting By Alternative Route of Administration

A study was performed to determine the effect of boosting by a route of administration that differs from the initial inoculation route of administration. Taconic Balb/c/ AnNTacfBR 3 week old male mice were anesthetized IP with 200 µl ketoset diluted 1:10 in PBS and inoculated IN with 50 µl undiluted virus, WRSV (VERO $350°_1$ Titer $2.00 \times 10^6$ Pfu's/ml in VERO cells), CRIa, CaBCV, 19H and Ca48V. Mice were boosted with 100 µl virus via footpad injection. Approximately three weeks later, mice were boosted with 200 µl half virus and half complete Freund's adjuvant intramuscularly. Approximately ten days later, mice were bled for serum. Neutralization titers were done in VERO cells in the presence of complement. The following table sets forth the results of the study.

TABLE 8

Neutralization Data in Presence of Complement (60% Reduction)

| Antiserum to: | Titer with Complement[+] |
|---|---|
| Normal Serum | |
| 19H | 1:160 |

TABLE 8-continued

Neutralization Data in Presence of Complement (60% Reduction)

| Antiserum to: | Titer with Complement[+] |
|---|---|
| CaBCV | 1:160 |
| Ca48V | >1:640 |
| CRIa | >1:640 |
| WRSV | >1:640 |

[+]Titer reported as last dilution with 60% reduction over positive controls with complement average positive control = 100.33 colonies/well.

F. Cytotoxicity Study

Generation of CTL. Spleens from two BALB/c mice from each group that were immunized with either live mouse adapted A2 virus, line 19H or placebo, (see A. above, Immunogenicity of RSV Lines (Study 1)), were removed three weeks after the booster dose. Single cell suspensions were prepared and incubated at $2.5 \times 10^7$ cells in RPMI 1640 plus 10% FBS. Gamma-irradiated (3,000 rads) syngeneic spleen cells were infected with RSV at an MOI of 1 for 2 h. The cells were washed twice to remove free virus and $2.5 \times 10^7$ spleen cells in a final volume of 10 ml of complete medium. CTL activity was tested 5–6 days following re-stimulation.

Cytoxicity assay. On the date of the assay, effector cells were washed twice with fresh medium and viable cell counts were determined by the Trypan blue dye exclusion method. BC cells ($2 \times 10^6$ cells), a BALB/c fibroblast cell line, as well as BCH4 cells ($2 \times 10^6$ cells), a BALB/c fibroblast T cell line persistently infected with RSV, were pulsed with 200 µCi of Sodium $^{51}$chromate (Dupont) for 90 min. The targets were washed three times with medium to remove free $^{51}$chromium. Viable cell counts of the target cells were determined and target cell suspensions were prepared at $2 \times 10^4$ cells/mL. Washed responder T-cells (in 100 µl) were incubated with $2 \times 10^3$ target cells (in 100 µl) at various Effector:Target cell ratios in triplicate in 96-well V-bottomed tissue-culture plates for 4 h at 37° C. with 6% $CO_2$. Spontaneous and total release of $^{51}$chromium were determined by incubating target cells with either medium or 2.5% Triton-X100 in the absence of responder lymphocytes. Six replicates of each were prepared. After 4 h plates were centrifuged at 200× g for 2 min and 100 µl supernatant was removed from each well to determine the amount of $^{51}$chromium released. Percentage specific $^{51}$chromium release was calculated as (Experimental Release—Spontaneous Release) (Total Release—Spontaneous Release)×100. The Spontaneous Release of $^{51}$chromium in the absence of effector cells was found to be between 10–15% in these studies.

FIG. 4 shows the results of the study. In FIG. 4, lysis of BC (filled symbols) and BCH4 (empty symbols) by CTL generated from BALB/c mice immunized with placebo (Triangle), live RSV (Square) or line 19H (Circle) is shown. Mice immunized with live RSV (empty square) or 19H (empty circle) lysed BCH4 cells (RSV infected) significantly at all effector to target cell ratios when compared to the lysis of BC (un-infected) cells. There was no significant levels of lysis by effector cells from the placebo indicating that line 19H is capable of inducing significant levels of CTL activity.

G. Protection Study

Generation of CTL. Spleens from two BALB/c mice from each group that were immunized with either the mutants or their respective progenitor viruses, live mouse adapted virus or medium (placebo) were removed three weeks after the booster dose. Single cell suspensions were prepared and incubated at $2.5 \times 10^7$ cells in RPMI 1640 plus 10% FBS. Gamma-irradiated (3,000 rads) syngeneic spleen cells were infected with RSV at an MOI of 1 for 2 h. The cells were washed twice to remove free virus and $2.5 \times 10^7$ spleen cells in a final volume of 10 mL of complete medium. CTL activity was tested 5–6 days following re-stimulation.

Cytotoxicity assay. On the day of the assay, effector cells were washed twice with fresh medium and were resuspended in 2 mL of complete medium. BC cells ($2 \times 10^6$ cells), a BALB/c fibroblast cell line, as well as BCH4 cells ($2 \times 10^6$ cells), a BALB/c fibroblast T cell line persistently infected with RSV, were pulsed with 200 µCi of Sodium $^{51}$chromate (Dupont) for 90 min. The targets were washed three times with medium to remove free $^{51}$chromium. Viable cell counts of the target cells were determined and target cell suspensions were pared at $2 \times 10^4$ cells/mL. Washed responder T-cells at various dilutions (in 100 µl) were incubated with $2 \times 10^3$ target cells (in 100 µl) in triplicate in 96-well V bottomed tissue-culture plates for 4 h at 37° C. with 6% $CO_2$. Spontaneous and total release of $^{51}$chromium were determined by incubating target cells with either medium of 2.5% Triton-X100 in the absence of responder lymphocytes. Six replicates of each were prepared. After 4 h plates were centrifuged at 200× g for 2 min. and 100 µl of supernatant was removed from each well to determine the amount of $^{51}$chromium related. Percentage specific $^{51}$chromium release was calculated as (Experimental Release-Spontaneous Release)/(Total release—Spontaneous release)×100. The spontaneous release of $^{51}$chromium in the absence of effector cells was found to be between 10–15% in these studies. The lysis in cultures is directly proportional to the number of effector cells present in the culture, which in turn is proportional to the number of CTL precursors activated in vivo by that particular immunogen.

The results of this cytotoxicity study are shown in FIG. 5. In FIG. 5, lysis of BC (open symbols) and BCH4 cells (filled symbols) by CTL generated from BALB/c mice immunized with either placebo, 19HL 3PI, 19H 3PI, 19H MD, wt 19, CRIa MD or WRSV, or live mouse adapted virus is shown. Mice immunized with live mouse adapted RSV, 19HL 3PI, 19H 3PI, 19H MD, CRIa MD, wt 19 and WRSV, lysed BCH4 cells (RSV infected) at all effector cell dilutions when compared to the lysis of BC (non-infected) cells. There were no significant level of lysis by effector cells from the placebo indicating that all the tested viruses are capable of inducing significant levels of CTL activity.

To evaluate the ability of the plaque purified deposited viruses to protect mice against live virus challenge, mice that were immunized with either the plaque purified viruses, progenitor viruses or medium alone (see D. above, Immunogenicity of RSV Lines (Study 4)), were challenged with $10^6$ pfu of RSV A2 immediately after the 8 week bleed. Lungs were harvested four days after virus challenge and virus titers in lung homogenates were determined by the plaque assay. As shown in the table below, mice immunized with the viruses of the present invention were protected against live virus challenge. The protective ability was comparable to that observed with mice that were inoculated with live mouse adapted virus.

TABLE 9

Protective Ability Of The Plaque Purified Viruses And Progenitor Viruses

| Virus | Mean Virus Lung Titre (log pfu/g ± s.d.)* | % Animals Protected |
|---|---|---|
| Placebo | 5.2 ± .06 | 0 |
| 19HL 3PI | ≦1.7 ± 0 | 100 |
| 19H 3PI | ≦1.7 ± 0 | 100 |
| 19H MD | ≦1.7 ± 0 | 100 |
| wt 19 | ≦1.7 ± 0 | 100 |
| CRIa MD | ≦1.7 ± 0 | 100 |
| WRSV | 1.9 ± 2.2 | 50 |
| Live virus | ≦1.7 ± 0 | 100 |

*Represents the mean value of 6 animals.

Specific Example 4

Sequence Analysis of the F Gene

A. Sequence Comparison—WRSV

In identifying the molecular basis for the ts phenotype, the F gene of the wild type (WRSV), line Ca19V and line 19H were sequenced using polymerase chain reaction (PCR). The F gene is composed of 1899 nucleotides, 13 of which are non-coding at the 3' end. Both viruses were grown in Vero cells to isolate the RNA for sequencing. Comparison of the F genes of line Ca19V and line 19H revealed 73 nucleotide and 15 amino acid differences. Comparison of the F genes of line 19H and WRSV revealed 72 nucleotide and 13 amino acid differences. There are 11 nucleotide changes and 6 amino acid changes between the F genes of the two line 19 attenuated viruses, Ca19V and 19H. Only base changes (no insertions or deletions) were found. The F genes of the two attenuated line 19 viruses have 66 nucleotides and 11 amino acids in common but differ from that of WRSV (amino acid positions 66, 76, 79, 97, 119, 129, 191, 357, 384, 522 and 530).

The Garnier Osguthorpe Robson (GOR) predicted F protein structures of the two line 19 viruses are nearly identical; however, the GOR F protein structure of WRSV differs at amino acid 97, 119,191, 357 and 522 from both attenuated viruses and differs at amino acid 294 only from line Ca19V. Amino acid 97 (threonine in both line 19's and methionine in WRSV) predicts a turn in the attenuated line 19 viruses not present in WRSV. Amino acid 119 (phenylalanine in both line 19's and leucine in WRSV) predicts an additional turn in the attenuated line 19 viruses not present in WRSV. Amino acid 191 (lysine in the attenuated lines 19 viruses and arginine in WRSV) predicts the formation of an alpha helix in the attenuated line 19 viruses while WRSV continues a beta sheet fold and then turns. Amino acid 357 predicts the formation of an alpha helix in WRSV not present in either attenuated line 19 virus and amino acid 522 predicts a turn in WRSV not present in either attenuated line 19 viruses. Amino acid 294 predicts the formation of a beta sheet in WRSV and 19H not present in Cal 9V. It is interesting that, although there are 6 amino acid differences between the two attenuated line 19 viruses, the 2 attenuated viruses have the same predicted protein fold whereas the WRSV fold is quite different. Thus, amino acids 97, 119, 191, 357 and 522 are good candidates for attenuating lesions in the F protein.

TABLE 10

Sequence Comparison of the Genes Coding for the F Proteins of WRSV, Ca19V and 19H

| Nucleotide # | WRSV | Ca19V | 19H | Amino Acid # | WRSV | Ca19V | 19H |
|---|---|---|---|---|---|---|---|
| 76 | C | T | T | | | | |
| 85 | T | C | C | | | | |
| 106 | A | G | G | | | | |
| *131* | *G* | *G* | *A* | 40 | Val | Val | Ile |
| 155 | C | T | T | | | | |
| 199 | T | C | C | | | | |
| 209 | A | G | G | 66 | Lys | Glu | Glu |
| 220 | T | C | C | | | | |
| 235 | T | C | C | | | | |
| 240 | T | C | C | 76 | Val | Ala | Ala |
| 250 | G | A | A | 79 | Met | Ile | Ile |
| 265 | T | C | C | | | | |
| 271 | T | C | C | | | | |
| 296 | T | C | C | | | | |
| 303 | T | C | C | <u>97</u> | Met | Thr | Thr |
| 322 | A | T | T | | | | |
| 352 | G | G | A | | | | |
| 368 | C | T | T | <u>119</u> | Leu | Phe | Phe |
| 370 | C | T | T | | | | |
| 398 | T | A | A | 129 | Leu | Ile | Ile |
| 430 | T | C | C | | | | |
| 457 | C | T | T | | | | |
| 505 | G | A | A | | | | |
| 511 | G | A | A | | | | |
| 514 | C | A | A | | | | |
| 541 | G | A | A | | | | |
| 585 | G | A | A | <u>191</u> | Ala | Lys | Lys |
| 604 | C | T | T | | | | |
| 622 | G | A | A | | | | |
| 623 | T | C | C | | | | |
| *716* | *A* | *G* | *C* | 235 | Arg | Gly | Arg |
| 718 | G | A | A | | | | |
| 763 | C | T | T | | | | |
| 787 | G | A | A | | | | |
| 871 | C | T | T | | | | |
| *893* | *G* | *A* | *G* | 294 | Glu | Lys | Glu |
| 898 | A | G | G | | | | |
| *906* | *C* | *C* | *A* | 298 | Ala | Ala | Glu |
| 959 | T | C | C | | | | |
| 961 | A | G | G | | | | |
| 1003 | A | C | C | | | | |
| 1015 | A | G | G | | | | |
| 1048 | T | C | C | | | | |
| 1057 | A | T | T | | | | |
| 1083 | A | C | C | <u>357</u> | Lys | Thr | Thr |
| 1087 | T | C | C | | | | |
| 1090 | A | G | G | | | | |
| *1116* | *A* | *T* | *A* | 368 | Asp | Val | Asp |
| 1126 | C | T | T | | | | |
| 1163 | G | A | A | 384 | Val | Ile | Ile |
| 1180 | C | C | T | | | | |
| *1206* | *C* | *T* | *C* | 398 | Ser | Leu | Ser |
| 1222 | C | T | C | | | | |
| 1228 | C | T | T | | | | |
| 1241 | C | C | T | | | | |
| 1246 | A | G | G | | | | |
| 1465 | C | A | A | | | | |
| 1501 | T | C | C | | | | |
| 1504 | G | A | A | | | | |
| 1519 | T | C | C | | | | |
| 1520 | T | C | C | | | | |
| 1576 | A | C | C | | | | |
| 1577 | A | G | G | <u>522</u> | Thr | Ala | Ala |
| 1603 | A | G | G | 530 | Ile | Met | Met |
| 1655 | C | T | C | | | | |
| 1669 | C | A | A | | | | |
| 1705 | G | A | A | | | | |
| 1739 | A | T | T | | | | |
| 1751 | C | T | T | | | | |
| 1781 | C | A | A | | | | |
| 1802 | Q | A | A | | | | |
| 1813 | T | C | C | | | | |
| 1829 | T | C | C | | | | |
| 1838 | A | G | G | | | | |
| 1841 | C | T | T | | | | |
| 1843 | T | C | C | | | | |
| 1847 | T | C | C | | | | |

Differences between Ca19V and 19H are italicized and bolded. Amino acids which impact on the predicted protein folds are underlined.

B. Sequence Comparison—wt 19

The nucleotide sequence of the F genes of line 19 wild type (wt 19), Ca19V and 19H, were compared by f-mol sequencing. The following table lists the nucleotide and amino acid changes in the F genes between lines Ca19V, 19H and wt 19.

TABLE 11

Sequence Differences Between The F Genes Of wt 19, Ca19V and 19H

| Nucleotide # | wt 19 | 19H | Ca19V | Amino Acid # | wt 19 | 19H | Ca19V |
|---|---|---|---|---|---|---|---|
| 131 | G | A | G | 40 | val | iso | val |
| 352 | A | A | G | | | | |
| 716 | C | C | G | 235 | arg | arg | gly |
| 893 | G | G | A | 294 | glu | glu | lys |
| 906 | C | A | C | 298 | ala | glu | ala |
| 1116 | A | A | T | 368 | asp | asp | val |
| 1180 | T | T | C | | | | |
| 1206 | C | C | T | 398 | ser | ser | leu |
| 1222 | T | C | T | | | | |
| 1241 | T | T | C | | | | |
| 1249 | C | A | A | | | | |
| 1655 | C | C | T | | | | |

Differences between 19H and wt 19 are bolded.
Differences between Ca19V and wt 19 are italicized.

Between wt 19 and 19H, there were 4 nucleotide differences, 2 of which coded for amino acid differences. Amino acid 40, valine in wt 19 and isoleucine in 19H, is a conserved change since both are hydrophobic and neither is charged. The difference at amino acid 298 is not conserved. Alanine, in wt 19, is hydrophobic and not charged while glutamic acid in 19H, is not hydrophobic and is negatively charged. Chou Fasman analysis predicts that the glutamic acid of 19H extends an alpha helix thus postponing the formation of a beta sheet predicted by the alanine at 298 of the wt 19 F protein.

Between wt 19 and Ca19V, there are 9 nucleotide differences and 4 amino acid differences, none of which is a conserved change. Amino acid 235 is basic arginine to uncharged glycine; amino acid 294 is negatively charged glutamic acid to positively charged lysine; amino acid 368 is negatively charged aspartic acid to hydrophobic valine; and amino acid 398 is uncharged serine to hydrophobic leucine. The structure of the two F proteins, as predicted by Chou Fasman, differs only at amino acid 234; Cal 9V extends an alpha helix, thus losing a turn predicted for the wt 19 F protein.

None of the amino acid differences is shared by the two line 19 attenuated viruses, but nucleotide 1249 (which does not code for an amino acid change) is C in wt 19 and A in both Ca19V and 19H.

Specific Example 5

Plaque Purification

As indicated above, several of the deposited strains were plaque purified. In particular, Line 19HL 3PI was passed 72 times in MRC5 cells, then plaque purified three times in Vero cells. Line 19H 3PI was passed 70 times in MRC5 cells, then plaque purified three times in Vero cells and passed 2 times in MRC5 cells. Line 19H MD was passed 92 times in MRC5 cells, then purified by limiting dilution three times. Line CRIa MD was passed 28 times at 25° C. and 1 time at 33° C. then purified by limiting dilution five times. The following table sets forth the titers of the strains at 33° C. and 39° C., illustrating temperature sensitivity.

TABLE 12

| | $TCID_{50}$ In MRC5 Cells | |
|---|---|---|
| Virus | 33° C. | 39° C. |
| 19HL 3PI | $1.0 \times 10^6$ | $1.0 \times 10^5$ |
| 19H 3PI | $3.2 \times 10^5$ | $2.0 \times 10^3$ |
| 19H MD | $3.2 \times 10^5$ | $1.0 \times 10^3$ |
| CRIa MD | $>1.0 \times 10^6$ | $2.0 \times 10^3$ |
| 19H | $3.16 \times 10^6$ | |
| 19H 4MD | $3.16 \times 10^4$ | |
| WRSV | $2.0 \times 10^5$ | $2.0 \times 10^5$ |

Specific Example 6

Human Studies

The attenuated virus of the present invention is administered to human subjects according to well established human RSV protocols, for example, those described in Wright et al., *Infect. Immun.* 37:397–400 (1982); Kim et al., *Pediatrics* 52:56–63 (1973) and Wright et al., *J. Pediatr.* 88:931–936 (1976). Briefly, adults or children are inoculated intranasally via droplet with $10^2$ to $10^9$ PFU, preferably $10^4$ to $10^5$ PFU, of attenuated virus per ml in a volume of 0.5 ml. Antibody response is evaluated by complement fixation, plaque neutralization, and/or enzyme-linked immunosorbent assay. Individuals are monitored for signs and symptoms of upper respiratory illness. Subsequent immunizations are administered periodically to the individuals as necessary to maintain sufficient levels of protective immunity.

The foregoing discussion discloses and describes merely exemplary embodiments of the present invention. One skilled in the art will readily recognize from such discussion, and from the accompanying claims, that various changes, modifications and variations can be made therein without departing from the spirit and scope of the invention as defined in the following claims.

All patents and other references cited herein are expressly incorporated by reference.

We claim:

1. An immunogenic composition comprising an attenuated respiratory syncytial virus selected from the group consisting of the viruses having ATCC Designation Nos. VR-2511, VR-2512, VR-2513, VR-2514, VR-2515, VR-2516, VR-2517, VR-2564, VR-2565, VR-2566, VR-2567, VR-2572, and derivative viruses of ATCC Designation Nos. VR-2570 and VR-2571, wherein the derivative viruses are characterized by having a codon encoding an amino acid in the F protein chosen from the group consisting of a codon encoding isoleucine at amino acid 40, a codon encoding glutamic acid at amino acid 66, a codon encoding alanine at amino acid 76, a codon encoding isoleucine at amino acid 79, a codon encoding threonine at amino acid 97, a codon encoding phenylalanine at amino acid 119, a codon encoding isoleucine at amino acid 129, a codon encoding lysine at amino acid 191, a codon encoding glycine at amino acid 235, a codon encoding arginine at amino acid 235, a codon encoding lysine at amino acid 294, a codon encoding glutamic acid at amino acid 294, a codon encoding glutamic acid at amino acid 298, a codon encoding alanine at amino acid 298, a codon encoding threonine at amino acid 357, a codon encoding valine at amino acid 368, a codon encoding aspartic acid at amino acid 368, a codon encoding isoleucine at amino acid 384, a codon encoding leucine at amino acid 398, a codon encoding serine at amino acid 398, a codon encoding alanine at amino acid 522, a codon encoding methionine at amino acid 530 and combinations thereof.

2. A method of inducing an immune response in a host against disease caused by infection by respiratory syncytial virus, comprising the step of administering to the host an immunoeffective amount of the vaccine composition of claim 1.

3. The composition of claim 1, wherein the virus is a derivative virus of VR-2570.

4. The composition of claim 1, wherein the virus is a derivative virus of VR-2571.

5. The method of claim 2, wherein the virus is a derivative virus of VR-2570.

6. The method of claim 2, wherein the virus is a derivative virus of VR-2571.

7. The method of claim 2, wherein the host is a human.

* * * * *